US008586529B2

(12) United States Patent
Saito et al.

(10) Patent No.: US 8,586,529 B2
(45) Date of Patent: Nov. 19, 2013

(54) COMPOSITION FOR PREVENTING AND IMPROVING METABOLIC SYNDROME

(71) Applicant: J-Oil Mills, Inc., Tokyo (JP)

(72) Inventors: Sanshirou Saito, Chuo-ku (JP); Toshiro Sato, Chuo-ku (JP); Syuichi Kamo, Chuo-ku (JP); Yousuke Isobe, Chuo-ku (JP)

(73) Assignee: J-Oil Mills, Inc., Tokyo (JP)

( * ) Notice: Subject to any disclaimer, the term of this patent is extended or adjusted under 35 U.S.C. 154(b) by 0 days.

(21) Appl. No.: 13/652,748

(22) Filed: Oct. 16, 2012

(65) Prior Publication Data

US 2013/0065821 A1 Mar. 14, 2013

Related U.S. Application Data

(62) Division of application No. 12/227,951, filed as application No. PCT/JP2007/062333 on Jun. 19, 2007, now abandoned.

(30) Foreign Application Priority Data

Jul. 31, 2006 (JP) ................................. 2006-208949

(51) Int. Cl.
*A61K 36/00* (2006.01)
*A61K 47/42* (2006.01)
*A61K 38/00* (2006.01)

(52) U.S. Cl.
USPC .............. 514/1.1; 435/415; 435/426; 426/44; 426/522; 530/350; 524/25

(58) Field of Classification Search
None
See application file for complete search history.

(56) References Cited

U.S. PATENT DOCUMENTS

| | | | |
|---|---|---|---|
| 3,653,912 A | 4/1972 | Koski et al. | |
| 5,792,852 A | 8/1998 | do Couto et al. | |
| 6,544,566 B1 | 4/2003 | Waggle et al. | |
| 7,560,131 B2 | 7/2009 | Wanezaki et al. | |
| 8,173,178 B1 * | 5/2012 | Ghaedian et al. | 424/725 |
| 2001/0026814 A1 | 10/2001 | Waggle et al. | |
| 2001/0029248 A1 | 10/2001 | Waggle et al. | |
| 2003/0139610 A1 * | 7/2003 | Khare et al. | 549/200 |
| 2004/0013791 A1 | 1/2004 | Singh | |
| 2004/0071800 A1 | 4/2004 | Waggle et al. | |
| 2004/0146627 A1 | 7/2004 | Beaver et al. | |
| 2005/0129832 A1 | 6/2005 | Hammond | |
| 2005/0214346 A1 * | 9/2005 | Bringe et al. | 424/439 |
| 2007/0003642 A1 | 1/2007 | Wanezaki et al. | |
| 2009/0186347 A1 * | 7/2009 | Cox et al. | 435/6 |
| 2011/0033941 A1 * | 2/2011 | Hess et al. | 436/86 |
| 2011/0237532 A1 * | 9/2011 | De Vries et al. | 514/27 |
| 2012/0058094 A1 * | 3/2012 | Blaser et al. | 424/93.41 |
| 2012/0264966 A1 * | 10/2012 | Miller et al. | 558/169 |

FOREIGN PATENT DOCUMENTS

| | | |
|---|---|---|
| JP | B2-07-025796 | 3/1995 |
| JP | A-2000-344676 | 12/2000 |
| JP | A-2003-088334 | 3/2003 |
| JP | A-2003-286180 | 10/2003 |
| JP | A-2005-237356 | 9/2005 |
| JP | A-2006-217900 | 8/2006 |
| WO | WO 03/077904 A1 | 9/2003 |

OTHER PUBLICATIONS

Leenen et al. (1993) Relative effects of weight loss and dietary fat modification on serum lipid levels in the dietary treatment of obesity., J. Lipid, vol. 34, pp. 2183-2191.*
Grundy et al. (2004) Definition of Metabolic Syndrome—Report of the National Heart, Lung, and Blood Institute/American Heart Association Conference on Scientific Issues Related to Definition, Circulation, vol. 109, pp. 433-438.*
Berhow et al. 2006) Complete Quantification of Group A and Group B Soyasaponins in Soybeans, Agric. Food Chem., vol. 54, No. 6, pp. 2035-2044.*
Song et al. (2003) Soy protein with or without isoflavones, soy germ and soy germ extract, and daidzein lessen plasma cholesterol levels in golden Syrian hamsters, Exp. Biol. Med (Maywood)., vol. 228, No. 9, pp. 1063-1068.*
Sugano et al., "The hypocholesterolemic action of the undigested fraction of soybean protein in rats," *Atherosclerosis*, 1988, vol. 72, pp. 115-122.
Sugano et al., "Cholesterol-Lowering Activity of Various Undigested Fractions of Soybean Protein in Rats," *The Journal of Nutrition*, 1990, vol. 120, pp. 977-985.
Song et al., "Soy Protein With or Without Isoflavones, Soy Germ and Soy Germ Extract, and Daidzein Lessen Plasma Cholesterol Levels in Golden Syrian Hamsters," *Society for Experimental Biology and Medicine*, 2003, vol. 228, No. 9, pp. 1063-1068.
Hu et al., "Quantification of the Group B Soyasaponins by High-Performance Liquid Chromatography," J. Agric. Food Chem., 2002, vol. 50, pp. 2587-2594.

* cited by examiner

*Primary Examiner* — Manjunath Rao
*Assistant Examiner* — Samuel Liu
(74) *Attorney, Agent, or Firm* — Oliff & Berridge, PLC

(57) ABSTRACT

A method for improving blood HDL/LDL cholesterol ratio, reducing blood triglyceride level, reducing blood sugar level, and/or reducing body weight, that includes ingesting a composition containing a concentrated soybean germ product. The soybean germ product includes soybean germ protein; 1.0% by weight or less of saponin relative to the total weight of the soybean germ product; and 0.5% by weight or less of isoflavone relative to the total weight of the soybean germ product.

9 Claims, 6 Drawing Sheets

FIG. 1

![Figure 1: SDS-PAGE gel showing molecular weight markers at 94,000; 67,000; 43,000; 30,000; 20,000; and 14,400 Da. Lanes: MOLECULAR WEIGHT MARKER, SOYBEAN, SOYBEAN COTYLEDON, SOYBEAN GERM.]

FIG. 2

![Figure 2: SDS-PAGE gel showing molecular weight markers at 94,000; 67,000; 43,000; 30,000; 20,000; and 14,400 Da. Lanes: MOLECULAR WEIGHT MARKER, SOYBEAN, SOYBEAN GERM PROTEIN (DRAFTED AT HIGH TEMPERATURE), SOYBEAN GERM PROTEIN (DRAFTED AT LOW TEMPERATURE).]

AVERAGE ± SD, n=8

F I G. 5
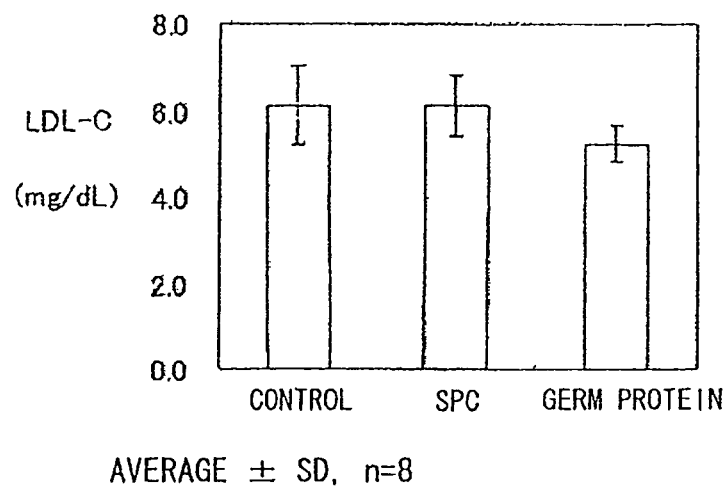
AVERAGE ± SD, n=8
F I G. 6
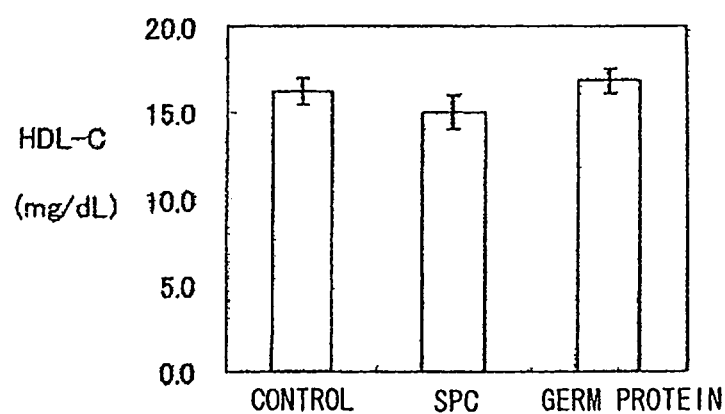
AVERAGE ± SD, n=8

F I G. 7
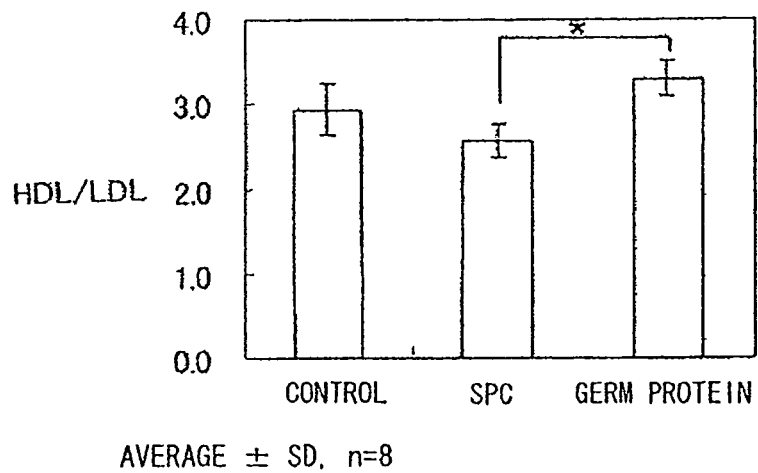
F I G. 8
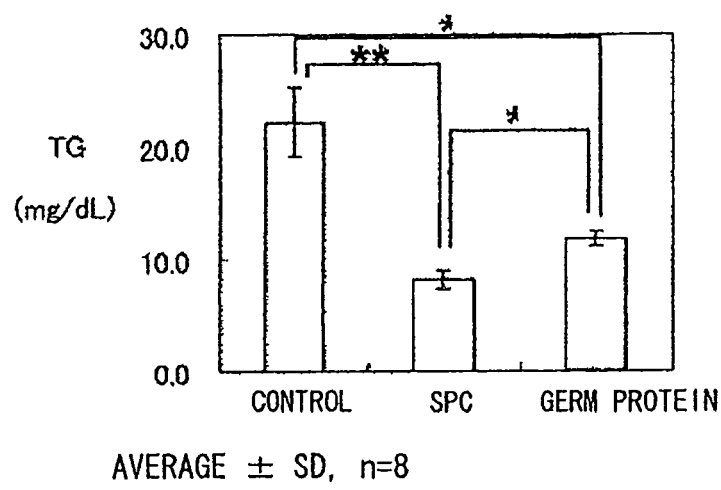

F I G. 9
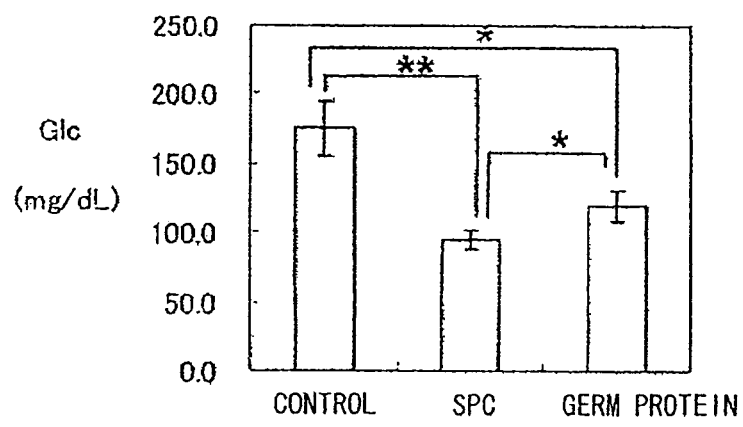
AVERAGE ± SD, n=8
F I G. 1 0
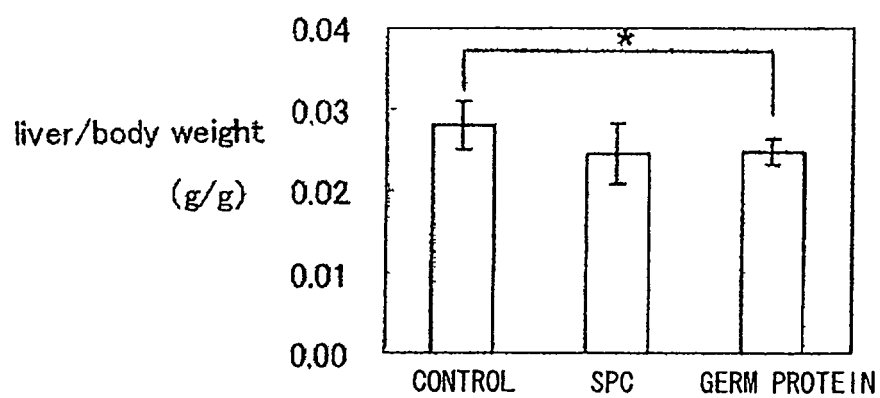
AVERAGE ± SD, n=8

F I G. 11
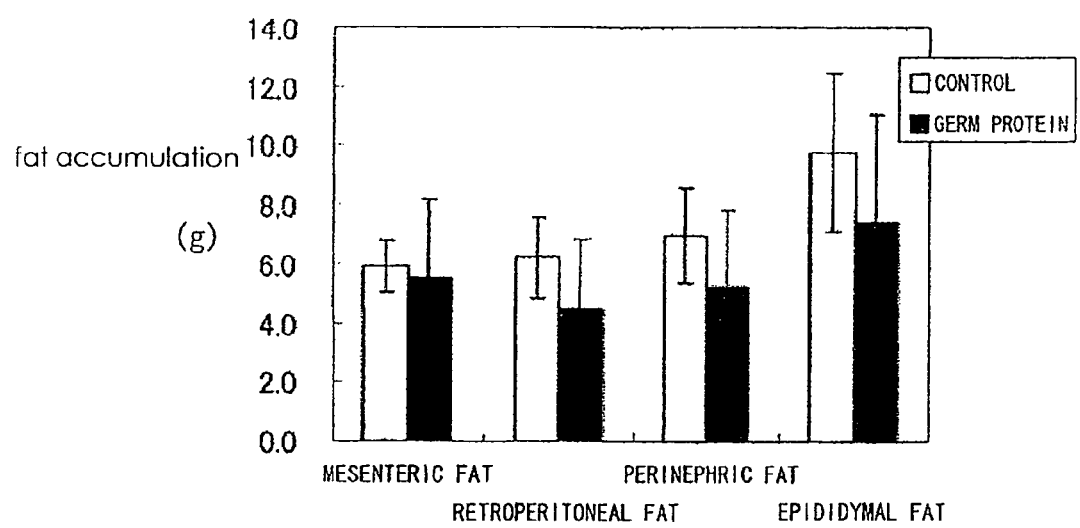
AVERAGE ± SD, n=8

COMPOSITION FOR PREVENTING AND IMPROVING METABOLIC SYNDROME

CROSS-REFERENCE TO PRIOR APPLICATIONS

This is a divisional of application Ser. No. 12/227,951 filed Dec. 3, 2008, which is a National Stage Application of PCT/JP2007/062333 filed Jun. 19, 2007, and claims the benefit of Japanese Application No. 2006-208949 filed Jul. 31, 2006. The entire disclosures of the prior applications are hereby incorporated by reference herein in their entirety.

BACKGROUND

The present invention relates to a composition for preventing and improving metabolic syndrome utilizing soy germ protein, more specifically to a composition for improving the blood lipid condition and the blood sugar level, controlling the increase in liver weight, and reducing the body weight.

In Japan, from ancient times, soybeans have been eaten in various forms, such as bean curd, soybean milk, deep-fat fried bean curd, boiled beans, fermented soybeans, soybean flour, miso (fermented soybean paste), and soy sauce. In recent years, various physiological components are receiving attention, so that soybean is expected to serve as food useful for health maintenance. Soybean protein (defatted soybean), which is prepared by removing oil from soybean, contains about 40 to 50% protein, and has relatively good amino acid balance of a vegetable protein. Therefore, soybean protein is called "field meat", and widely used for food and feed applications. Functional components contained in soybeans, such as isoflavone, lecithin, and vitamin E are also receiving attention, and these useful components have been used as supplements for, for example, prevention of various diseases. However, soybeans also contains a trypsin inhibitor which inhibits the activity of proteolytic enzymes, an antigenic protein as an allergen which causes an allergy, phytic acid which inhibits absorption of minerals and the like. Effective use of soybean as a nutritional functional food is based on two main points of efficient use of useful components and reduction of antinutrient components.

On the other hands, in recent years, metabolic syndrome has become a significant public health issue particularly among people of middle and advanced age, and food and drugs for improving the syndrome have been demanded. It is well known that soybeans reduce the blood cholesterol level. The effect is likely due to that soybean protein specifically binds to cholesterol precursors such as bile acid, and is excreted as feces.

In order to investigate the physiological functions such as the cholesterol reducing effect, identification of functional fractions of peptide components obtained from decomposed soybean protein has been studied. For example, it is confirmed that undigested fractions obtained by enzymatic digestion of soybean protein lower the cholesterol level (Patent Document 1, Non-patent Documents 1 and 2). As other soybean components which improve the blood neutral lipid, cholesterol and blood sugar levels, 11S globulin called glycinin (Patent Document 2), 7S globulin called β-conglycinin, isoflavone, and others are said to be effective, but no clear conclusion has been provided. Further, proteins of soybean germ have little been studied.

Regarding the substances derived from soybean germ, it is reported that isoflavone aglycon, which is contained in a substance prepared by treating soybean germ with *aspergillus oryzae*, hydrolyzing the product, and extracting and concentrating the product with a solvent, is effective as an active ingredient for promoting bioactivity (Patent Document 3). However, there still are different opinions among researchers about the efficacy of isoflavone inclusive of its metabolites, so that no clear conclusion has been provided.

The protein composition of soybean germ is markedly different from that of soybean. Soybean germ has a low nutritional value because it contains little storage protein such as conglycinin and β-conglycinin, and its total protein content is low. In addition, soybean germ abundantly contains antinutrients such as saponin and allergens, so that its excessive ingestion causes an allergy, growth inhibition or the like. Soybean germ further has a bad flavor. Therefore, it is believed to be unsuitable for uses in foods, beverages, and medicines. The inventors have applied for a patent on a soybean germ protein composition which resolves the problem (Japanese Patent Application No. 2005-36942). The composition is prepared by removing antinutrient components from soybean germ through solvent treatment in combination with heat treatment. The process increases the content of soybean germ protein while decreasing the content of allergens derived from the protein, and improves the flavor. However, functionality of soybean germ protein, more specifically, processing characteristics and physiological effects caused by the ingestion of the protein have not known at all until the completion of the present invention.

Patent Document 1: Japanese Patent Publication No. 07-025796
Patent Document 2: Japanese Patent Application Laid-Open No. 2003-88334
Patent Document 3: WO 2003/077904
Non-patent Document 1: Atherosclerosis, 72, 115, 1988
Non-patent Document 2: J. Nutr., 120, 977, 1990

SUMMARY

The present invention is intended to identify a functional component of soybean having the effect of improving the blood lipid and blood sugar levels, which has not been revealed, and utilize the component in food, beverages, drugs or a material thereof.

An aspect of the present invention is a composition for improving blood lipid level and blood sugar level, an active ingredient of the composition being a fraction containing soybean germ protein obtained through fractionation carried out such that the fraction contains germ protein, which is a minor element of soybeans, at a ratio of 20% or more, more preferably 40% or more. Further, when the obtained soybean germ protein is subjected to, for example, solvent treatment, chemical treatment, or physical treatment thereby removing antinutrient components, and in combination with heat treatment, the protein content in the resultant soybean germ protein increases while the content of allergens derived from the protein decreases, and the flavor of the protein is improved.

More specifically, the present invention is directed to a composition for improving blood HDL/LDL cholesterol ratio, reducing blood triglyceride level, reducing blood sugar level, and reducing body weight, the composition containing soybean germ protein as an active ingredient.

The composition according to the present invention improves blood cholesterol level, triglyceride and blood sugar level, thereby contributing to health promotion.

BRIEF DESCRIPTION OF THE DRAWINGS

FIG. 1 is a view showing electrophoretic patterns of proteins.

FIG. 2 is a view showing electrophoretic patterns of defatted proteins.

FIG. 5 is a graph showing the change in blood LDL cholesterol concentration after administration of germ protein and SPC.

FIG. 6 is a graph showing the change in blood HDL cholesterol concentration after administration of germ protein and SPC.

FIG. 7 is a graph showing the change in blood HDL cholesterol/blood LDL cholesterol ratio after administration of germ protein and SPC.

FIG. 8 is a graph showing the change in blood triglyceride concentration after administration of germ protein and SPC.

FIG. 9 is a graph showing the change in blood sugar level after administration of germ protein and SPC.

FIG. 10 is a graph showing the change in liver weight per body weight after administration of germ protein and SPC.

FIG. 11 is a graph showing the change in total blood cholesterol concentration after administration of germ protein and SPC.

DETAILED DESCRIPTION

Figure 3:
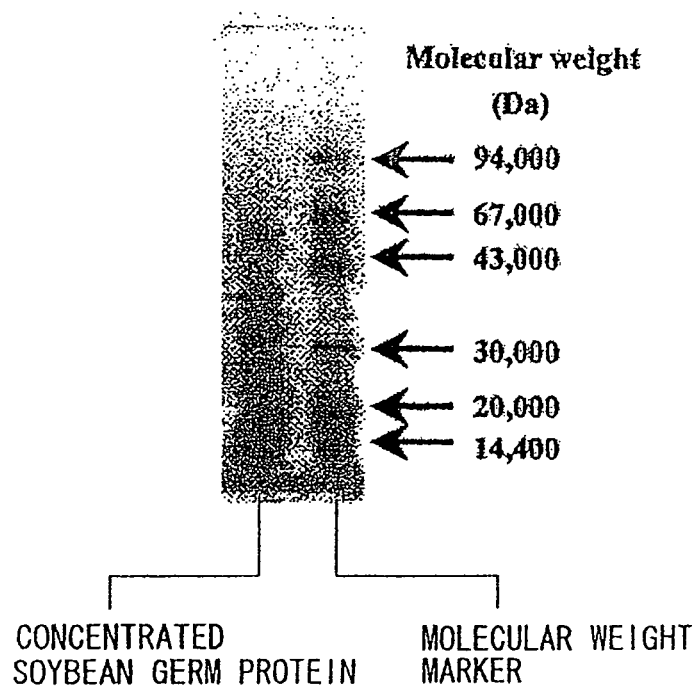
FIG. 3 is a view showing electrophoretic patterns of a concentrated soybean germ protein.

Common soybean contains about 0.8% soybean germ protein, though the content varies among species. Isolation of soybean germ protein from soybean may employ any method. For example, soybean may be half-crushed, and sieved to obtain soybean germ. Under the method, the soybean germ protein is concentrated to about 50-fold. The concentrate may be further defatted thereby removing the lipid component to increase the concentration of the soybean germ protein. Alternatively, the protein may be extracted with water or any organic solvent, preferably hydrous alcohol at 0° C. to 100° C. When the extracted soybean germ protein is heated at 50 to 300° C. for 1 to 180 minutes, soybean germ protein having an excellent flavor and a high nutritional value is obtained. If the heat treatment is carried out at a temperature lower than 50° C. and/or for a period of less than 1 minute, modification of the protein is insufficient, and if the temperature is higher than 300° C. and/or the period is more than 180 minutes, the protein is burned and the amino acids decrease. According to a method of removing the antinutrient components from soybean germ through extraction with an aqueous solvent and then collecting specific proteins by isoelectric precipitation under pH control with an acid or alkali, extraction and collection can be carried out with simple equipment. Alternatively, according to a method of extracting and removing low polarity substances using supercritical carbon dioxide, carbon dioxide is vaporized in a state that it is returned to normal temperature and normal pressure conditions, which advantageously dispenses with subsequent drying treatment.

In the present invention, the solvent treatment and heat treatment may be performed sequentially or simultaneously, or either one treatment may be dispensed with. They may be combined with other treatment processes such as pulverization, separation, and chromatography. The soybean germ protein of the present invention may be produced from common soybean protein such as defatted soybean, soybean protein concentrate, soybean protein isolate, and soybean milk through removal of storage protein specifically abundant in the cotyledon of soybean, and fibers abundant in seed coat. The germ portion of soybean contains isoflavone and saponin at relatively high concentrations, so that excess intake of the germ needs to be careful of. However, combination of the above methods provides soybean germ protein which contains less isoflavone and saponin, and can safely be taken.

For example, when soybean germ is subjected to solvent treatment with hexane and/or hydrous alcohol, and heat treatment at 50 to 300° C. for 1 to 80 minutes, the isoflavone content is decreased to 0.5% or less, and the saponin content is decreased to 1% or less. More specifically, when soybean germ is subjected to solvent treatment with 70% ethanol at 70° C. for 30 minutes, and heat treatment at 100° C. for 40 minutes, the isoflavone content is decreased to about 0.1%, and the saponin content is decreased to about 0.2%.

The obtained soybean germ protein is markedly different from the protein composition of ordinary soybean, and thus can be readily identified by SDS-PAGE analysis.

The soybean germ protein obtained according to the present invention has the following effects.

Firstly, the soybean germ protein of the present invention is superior to casein and soybean protein in the effects of reducing the blood LDL cholesterol and increasing the blood HDL cholesterol, and in the effect of improving the blood HDL/LDL cholesterol ratio. In addition, the soybean germ protein prevents fat accumulation in organs thereby preventing metabolic syndrome. The effects are intrinsic to the soybean germ protein and are not found in soybean protein concentrate.

Secondly, the soybean germ protein of the present invention has the effect of reducing the blood triglyceride.

Thirdly, the soybean germ protein of the present invention has the effect of reducing the blood sugar level.

Fourthly, the soybean germ protein of the present invention has the effect of suppressing accumulation of body fat such as visceral fat, and reducing the body weight.

In the form of known soy products, the content of germ protein is so low that the above-described effects achieved by the present invention cannot be obtained. However, physiological action can be provided by increasing the concentration of the germ protein according to the present invention. More specifically, the effects are achieved by an ingestion of about 0.05 g to 50 g of the soybean germ protein of the present invention per day, so that the protein can be added to various food or beverages.

The soybean germ protein according to the present invention may be used alone as an active ingredient, or in the form of, for example, a solid, liquid, sol, gel, or plastic composition containing a cereal powder such as starch, oils and fats, emulsifying agent, fragrant material, or thickener according to the requirements of the end product (e.g., drug, functional food, dietary supplement, food, or drink).

Examples of the starch include corn starch, waxy corn starch, high amylose corn starch, potato starch, wheat starch, tapioca starch, green bean starch, sago starch, rice starch, pea starch, and processed products of these starches prepared by subjecting a starch to single or combined physical or chemical treatment such as esterification treatment, etherification treatment, crosslinking treatment, acid treatment, oxidation treatment, heat-moisture treatment, and gelatinization treatment.

Examples of the oils and fats include soy oil, soybean germ oil, rapeseed oil, high oleic rapeseed oil, corn oil, sesame oil, sesame salad oil, perilla oil, linseed oil, peanut oil, safflower oil, high oleic safflower oil, sunflower oil, high oleic sunflower oil, high linolic sunflower oil, mid oleic sunflower oil, cottonseed oil, grape seed oil, macadamia nut oil, hazelnut oil, walnut oil, pumpkin seed oil, camellia oil, tea seed oil, olive oil, rice bran oil, wheat germ oil, palm oil, palm olein, palm kernel oil, coconut oil, cacao butter, algae oil, and hydrogenated oil, interesterified oil, and fractionated oil of these oils. These oils may be used alone or in combination of two or more of them.

The emulsifying agent may be one commonly used for food. Examples of the emulsifying agent include glycerin fatty acid ester, glycerin organic acid ester, sorbitan fatty acid ester, propylene glycol fatty acid ester, polyglycerin fatty acid ester, polyglycerin-condensed ricinolate, sucrose fatty acid ester, calcium stearoyl lactate, alkyl glycosides, erythritol fatty acid esters, polyoxyethylene sorbitan fatty acid esters, lecithin, enzymatically decomposed lecithin, and enzymatically modified lecithin. These emulsifying agents may be used alone or in combination of two or more of them.

The fragrant material may be a natural or synthetic fragrant material commonly used in foods.

The thickener increases the viscosity of the aqueous solution, and examples thereof include polysaccharides such as gum arabic, arabino galactan, guar gum, xanthan gum, psyllium seed gum, gellan gum, Tara gum, locust bean gum, tamarind seed gum, water-soluble soy polysaccharide (hemicellulose), sodium alginate, pullulan, pectin, karaya gum, ghatti gum, gum tragacanth, curdlan, glucomannan, chitin, chitosan, microfibrillar cellulose, and microcrystalline cellulose.

Examples of other additives include protein-derived substances such as collagen peptide, lactoprotein peptide, casein peptide, oligopeptide, whey protein concentrate, pea protein and gelatin, fibers such as soy fiber and pea fiber, and dextrin such as highly branched cyclic dextrin.

In addition, a pH adjuster and a saccharide may be added to the soybean germ protein.

Examples of the pH adjuster include lactic acid, gluconic acid, succinic acid, fumaric acid, citric acid, L-malic acid, DL-malic acid, glacial acetic acid, glucono delta lactone, L-tartaric acid, and DL-tartaric acid.

Examples of the saccharide include glucose (grape sugar), maltose, fructose (fruit sugar), galactose, trehalose, oligosaccharide, sucrose, and sorbit.

When the soybean germ protein of the present invention is contained in a baked confectionery such as cookie with a content of 1 to 50%, the baked confectionery has crispness which cannot be achieved with a common soybean protein, and gives a good smell and a good flavor.

The soybean germ protein of the present invention complements the flavor of food when it is mixed with a grain such as barley, wheat, rice, Japanese millet, foxtail millet, brown rice, black bean, red rice, green rice, red bean, black bean, red kidney bean, chicpea, white kidney bean, or the germ portion of these beans, or a seed such as peanut, walnut, sesame, pine nut, or chestnut. In addition, the soybean germ protein is suitable for, for example, cereals, baked confectionery, and energy bars owing to its physiological functionality.

EXAMPLES

The present invention is described in detail with reference to the following examples, but the scope of the present invention is not limited to the examples.

Test Example 1

Preparation 1 of Soybean Germ Protein

Soybeans were mechanically crushed, and sieved to obtain a concentrated fraction of soybean germ protein containing 70% or more of soybean germ. The concentrated fraction obtained by the method was subjected to total nitrogen analysis, and confirmed to have a total protein content of 40%. 70% or more of the protein was derived from soybean germ, so that the content of the soybean germ protein in the product was 28% or more, and the concentration factor was 35-fold or more. The protein composition of the sample was analyzed by SDS-PAGE. In the SDS-PAGE analysis, 1 g of the obtained sample was suspended in 5 ml of a 10 mM phosphate buffered saline (PBS: 8.2 mM $Na_2HPO_4$, 1.8 mM $KH_2PO_4$, 137 mM NaCl, 3 mM KCl), and subjected to ultrasonic treatment for 30 minutes to conduct extraction. 50 µl of the extract was dissolved in 250 µl of 50 mM Tris-HCl buffer containing 35 mM sodium dodecyl sulfate and 1% β-mercaptoethanol, and filtered through a MILLEX-HV 0.22 µm disposable filter to obtain a soluble protein sample. The sample was mixed with 20 µl of a 10% glycerol solution containing 1% bromophenol blue, and subjected to boiling treatment for 5 minutes in a boiling water bath to obtain a sample for electrophoresis. In the above treatment, the addition of β-mercaptoethanol is an important step, because the electrophoretic patterns markedly differ according to whether β-mercaptoethanol is added or not.

Electrophoresis was carried out using PhastSystem (Pharmacia LKB Biotechnology). The electrophoresis gel was PhastGel, Gradient 10-15, and staining was carried out with coomassie brilliant blue (CBB). After the electrophoresis, the stained polypeptide bands isolated by SDS-PAGE were analyzed with a chromatoscanner CS9300 (manufactured by Shimadzu Corporation) thereby measuring the absorption at 560 nm. Ordinary soybeans show a strong band in the vicinity of 33 kD, while the soybean germ protein shows a strong band in the vicinity of 30 kD. Similarly, ordinary soybeans show a strong band in the vicinity of 48 kD, while the soybean germ protein shows a characteristic strong band in the vicinity of 52 kD, and shows bands in the vicinity of 21 kD and 35 kD, which are not shown by the ordinary soybean protein. The image was graphed by the chromatoscanner, and the peak areas in the graph indicated that the bands of the soybean germ protein were stronger than those of the ordinary soybean protein.

The electrophoretic patterns of the proteins are shown in FIG. 1.

Test Example 2

Preparation 2 of Soybean Germ Protein

Soybeans were mechanically crushed, and sieved to obtain a fraction containing 70% or more of soybean germ. The fraction was defatted through hexane extraction at low and high temperatures, which is a common procedure for an oil pressing process, to obtain a soybean germ protein fraction. The soybean germ protein obtained by the above method was subjected to total nitrogen analysis, and found to have a total protein content of 43%, a soybean germ protein content of 30% or more, and a concentration factor of 37-fold or more. The protein composition of the sample was analyzed by SDS-PAGE. In the SDS-PAGE analysis, 1 mg of the obtained sample was suspended in 5 ml of a 10 mM phosphate buffered saline (PBS: 8.2 mM $Na_2HPO_4$, 1.8 mM $KH_2PO_4$, 137 mM NaCl, 3 mM KCl), and subjected to ultrasonic treatment for 30 minutes to conduct extraction. 50 µl of the extract was dissolved in 250 µl of 50 mM Tris-HCl buffer containing 35 mM sodium dodecyl sulfate and 1% β-mercaptoethanol, and filtered through a MILLEX-HV 0.22 µm disposable filter to obtain a soluble protein sample. The sample was mixed with 20 µl of a 10% glycerol solution containing 1% bromophenol blue, and subjected to boiling treatment for 5 minutes in a boiling water bath to obtain a sample for electrophoresis.

Electrophoresis was carried out using PhastSystem (Pharmacia LKB Biotechnology). The electrophoresis gel was PhastGel, Gradient 10-15, and staining was carried out with CBB. After the electrophoresis, the stained polypeptide bands isolated by SDS-PAGE were analyzed with a chromatoscanner CS9300 (manufactured by Shimadzu Corporation) thereby measuring the absorption at 560 nm. Ordinary soybeans show a strong band in the vicinity of 33 kD, while the soybean germ protein shows a strong band in the vicinity of 30 kD. Similarly, ordinary soybeans show a strong band in the vicinity of 48 kD, while the soybean germ protein shows a characteristic strong band in the vicinity of 52 kD, and show bands in the vicinity of 21 kD and 35 kD, which are not shown by the ordinary soybean protein. The image was graphed by the chromatoscanner, and the peak areas in the graph indicated that the bands of the soybean germ protein were stronger than those of the ordinary soybean protein.

The electrophoretic patterns of the defatted proteins are shown in FIG. 2.

Test Example 3

Preparation 3 of Soybean Germ Protein

Soybeans were mechanically crushed, and sieved to obtain a fraction containing 90% or more of soybean germ. The fraction was subjected to hexane extraction in a common procedure for an oil pressing process. Subsequently, 70% hydrous ethanol was added to the fraction, the mixture was stirred at 70° C. for 30 minutes, and then filtered to collect the residue. The residue was subjected to heat treatment at 100° C. for 40 minutes under reduced pressure to obtain a soybean germ protein fraction. The soybean germ protein obtained by the method was subjected to total nitrogen analysis, and found to have a total protein content of 62%, a soybean germ protein content of 56% or more, and a concentration factor of 70-fold or more. The sample was analyzed by SDS-PAGE in the same manner as Test Example 1, and found to have a characteristic composition of soybean germ protein in which the band in the vicinity of 30 kD was stronger than that in the vicinity of 33 kD, the band in the vicinity of 52 kD was stronger than that in the vicinity of 48 kD, and other bands were shown in the vicinity of 21 kD and 35 kD.

Further, antigenicity to bovine antiserum which was obtained using soybean protein as an antigen was measured by ELISA, and found to be 40 U/10 mg or less. The isoflavone content and saponin content were 0.5% or less, which are one-fifth or less of those in an ordinary soybean germ, and lower than those in whole soybeans. Therefore, high intake of the soybean germ protein will not cause bitterness or a problem of excess intake of these trace components. FIG. 3 shows an electrophoretic pattern of the concentrated soybean germ protein.

Analysis of Isoflavone and Saponin Contents

The isoflavone and saponin contents in the soybean germ proteins obtained in Test Examples 1 to 3 were measured.

Isoflavone content was analyzed according to a method based on the soy isoflavone food standard established by Japan Health Food & Nutrition Food Association, and the isoflavone content was determined in terms of aglycon.

The saponin content was analyzed by the following method. A sample containing about 10 mg of soy saponin was weighed, and refluxed at 80° C. for 2 hours in 5 ml of a 10% hydrogen chloride-methanol test solution. Insoluble matter was removed from the solution by centrifugation and filtration, and then the solution was analyzed by HPLC. As standard substances for quantitation, 10 mg each of soyasapogenol A and soyasapogenol B manufactured by Koshiro Company Limited were dissolved respectively in 100 ml of ethanol, and the solutions were used. HPLC used ODS columns, and the absorption at UV 210 nm was measured under the conditions of mobile phase:
  acetonitrile/water/methanol (6:3:1);
  flow rate: 0.7 ml/min; and
  temperature: 45° C.

The integrated value of the sample was compared with that of the standard substances, and the saponin content was determined in terms of aglycon. The results are shown in Table 1.

TABLE 1

Isoflavone and saponin contents in soybean germ protein

| | Protein content | Isoflavone content | Saponin content |
|---|---|---|---|
| Test Example 1 | 40.0% | 1.8% | 1.7% |
| Test Example 2 | 43.2% | 2.2% | 2.1% |
| Test Example 3 | 62.2% | 0.18% | 0.33% |

Example 1

High fat diets were fed to rats. The concentrations of various physiological substances in the blood were compared among rats fed with casein, with soybean protein concentrate (hereinafter abbreviated as SPC) as other common soybean protein or with the soybean germ protein of Test Example 3 (hereinafter abbreviated as germ protein).

Three diets prepared were: 1. casein diet, 2. SPC diet and 3. germ protein diet. The compositions of these diets are summarized in Table 2.

The germ protein was in the form of powder.

CD (SD) IGS male rats aged nine weeks were placed in individual cages, and preliminarily bred with a purified diet (AIN93G) for one week. Before starting the main test, the rats were grouped into three divisions each containing eight rats such that the divisions have an equal average body weight. The rats of the respective divisions were fed with 1. casein diet (control), 2. SPC diet containing SPC in place of casein, or 3. germ protein diet containing germ protein in place of casein. The test period was 28 days, and water and the diets were freely ingested. The test was carried out in an animal room under the following conditions: temperature, 22±3° C.; humidity, 60±15%; frequency of ventilation, 12 to 15 times/hour; and photoperiod, 12 hours (7 to 19 o'clock).

The rats were fasted for 18 hours from the evening of the last day of administration, and the blood was collected from the aorta abdominal is under ether anesthesia. The blood was taken in blood-collecting vessels containing a serum separating medium, and the vessels were centrifuged at 3000 rpm for 15 minutes to separate the serum. The serum was assayed for the levels of total cholesterol (FIG. 4), LDL cholesterol (FIG. 5), HDL cholesterol (FIG. 6), triglyceride (FIG. 8), and blood sugar level (FIG. 9). Further, the HDL cholesterol/LDL cholesterol ratio was calculated from the LDL cholesterol and HDL cholesterol levels (FIG. 7). After blood collection, the rats were exsanguinated to death, their livers were harvested and weighed. Further, mesenteric fat, retroperitoneal fat, perinephric fat and epididymal fat were isolated from the rats of the casein diet group and germ protein diet group to study the accumulation of fats. The measurement values were expressed by average±standard deviation. In the statistical analysis, Tukey multiple comparison test was carried out as necessary, and the significant differences between the measurement values were examined.

TABLE 2

Composition of rat diets (unit: %)

| Ingredients | Casein diet | SPC diet | Germ protein diet |
|---|---|---|---|
| Casein | 20.0000 | — | — |
| SPC | — | 25.6716 | — |
| Germ protein | — | — | 28.1967 |
| L-cystine | 0.30 | 0.30 | 0.30 |
| Lard | 35 | 35 | 35 |
| Corn starch | 19.9486 | 14.2770 | 11.7519 |
| Sucrose | 15 | 15 | 15 |
| Cellulose powder | 5 | 5 | 5 |
| AIN-93G mineral mixture | 3.50 | 3.50 | 3.50 |
| AIN-93G vitamin mixture | 1.00 | 1.00 | 1.00 |
| Choline bitartrate | 0.25 | 0.25 | 0.25 |
| Tertiary butyl hydroquinone | 0.0014 | 0.0014 | 0.0014 |

FIGS. 4 to 11 indicate the following.

Figure 4:
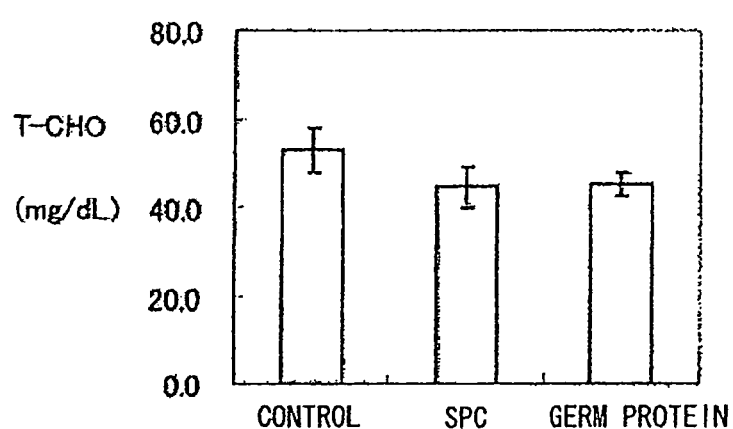
FIG. 4 is a graph showing the change in total blood cholesterol concentration after administration of germ protein and soybean protein concentrate (SPC).

FIG. 4 indicates that the germ protein diet decreases the total blood cholesterol.

FIG. 5 indicates that the germ protein diet decreases the blood LDL cholesterol.

FIG. 6 indicates that the germ protein diet increases the blood HDL cholesterol.

FIG. 7 indicates that the germ protein diet increases the blood HDL/LDL cholesterol ratio more than the casein diet, and that the germ protein diet significantly increased the HDL/LDL ratio in comparison with the SPC diet (P<0.05). The germ protein diet also significantly increased the cholesterol ratio in terms of HDL/total cholesterol in comparison with the SPC diet.

FIG. 8 indicates that the SPC and germ protein diets significantly decreased the blood triglyceride in comparison with the casein diet (P<0.05).

FIG. 9 indicates that the SPC and germ protein diets significantly decreased the blood sugar level in comparison with the casein diet (P<0.01 and P<0.05 for the SPC and germ protein diets, respectively).

FIG. 10 indicates that only the germ protein diet significantly decreased the liver weight per body weight in comparison with the casein diet (P<0.05), which demonstrates that the germ protein diet is effective in prevention of fatty liver.

FIG. 11 indicates that the accumulation of the mesenteric fat, retroperitoneal fat, perinephric fat and epididymal fat was smaller in weight in the division fed with the germ protein diet than the division fed with the casein diet, which shows that the germ protein diet suppresses accumulation of fats.

The above facts indicate that the germ protein diet decreased the blood triglyceride and blood sugar level in comparison with the casein diet. In addition, the germ protein diet improved the HDL/LDL cholesterol ratio and HDL/total cholesterol ratio in comparison with SPC, showing that it prevents lipid accumulation in the liver. Accordingly, it was proved that the germ protein of the present invention has physiological function different from that of ordinary soybean protein.

Example 2

Baked confectionery was made using the soybean germ proteins of Test Examples 1, 2, and 3 as soybean protein materials. As a comparative example, commercial separated soybean protein was used in place of the soybean germ proteins. The ingredients are as follows.

| Weak flour | 130 g |
|---|---|
| Butter | 100 g |
| Soybean protein material | 100 g |
| Sugar | 80 g |
| Egg | 1 |
| Vanilla essence | few drops |

An appropriate amount of milk was added to and mixed with the above ingredients. The dough was preserved at 4° C. for 2 hours, shaped into disks having a diameter of about 3 cm, and baked in an oven at 170° C. for about 12 minutes to make cookies. The cookies were tasted, and evaluated by sensory test by ten panelists. As a result of the sensory test, the cookies made of the soybean germ protein were more fragrant and crisp than those made of the separated soybean protein, and thus achieved higher scores in terms of flavor, texture, and taste.

TABLE 3

Result of sensory test (fractional components are rounded off)

| | Fragrance | Crispness | Taste |
|---|---|---|---|
| Test Examples 1 | 3 | 4 | 3 |
| Test Examples 2 | 4 | 5 | 4 |
| Test Examples 3 | 5 | 5 | 5 |
| Comparative Example | 2 | 2 | 1 |

5: very good;
4: good;
3: normal;
2: not good;
1: bad

What is claimed is:

1. A method for increasing blood HDL/LDL cholesterol ratio, reducing blood triglyceride level, reducing blood sugar level, or reducing body weight of a subject in need thereof, the method comprising administering to the subject a composition comprising a concentrated soybean germ product, the soybean germ product comprising: at least 28% by weight of soybean germ protein; 1.0% by weight or less of saponin relative to the total weight of the soybean germ product; and 0.5% by weight or less of isoflavone relative to the total weight of the soybean germ product.

2. The method of claim 1, wherein the concentrated soybean germ product is obtained by a process comprising solvent treating and heat treating soybean germ.

3. The method of claim 1, wherein the amount of the soybean germ protein in the concentrated soybean germ product is from 28% to 56% by weight.

4. The method of claim 1, wherein a daily amount of the composition administered contains a total of 0.05 g to 50 g of the soybean germ protein.

5. A method for reducing body weight of a subject in need thereof, the method comprising administering to the subject a composition comprising a concentrated soybean germ product, the soybean germ product comprising: at least 28% by weight of soybean germ protein; 1.0% by weight or less of saponin relative to the total weight of the soybean germ product; and 0.5% by weight or less of isoflavone relative to the total weight of the soybean germ product.

6. The method of claim 5, wherein the concentrated soybean germ product is obtained by a process comprising solvent treating and heat treating soybean germ.

7. The method of claim 5, wherein the concentrated soybean germ product contains at least 28% by weight of the soybean germ protein.

8. The method of claim 5, wherein the amount of soybean germ protein in the concentrated soybean germ product is from 28% to 56% by weight.

9. The method of claim 5, wherein a daily amount of the composition administered contains a total of 0.05 g to 50 g of the soybean germ protein.

\* \* \* \* \*